(12) United States Patent
Yuasa

(10) Patent No.: US 8,855,746 B2
(45) Date of Patent: Oct. 7, 2014

(54) ENDOSCOPIC MEDICAL TOOL AND MEDICAL SYSTEM

(75) Inventor: Masaru Yuasa, Tokyo (JP)

(73) Assignee: Olympus Medical Systems Corp. (JP)

( * ) Notice: Subject to any disclaimer, the term of this patent is extended or adjusted under 35 U.S.C. 154(b) by 729 days.

(21) Appl. No.: 12/534,178

(22) Filed: Aug. 3, 2009

(65) Prior Publication Data

US 2010/0063345 A1  Mar. 11, 2010

(30) Foreign Application Priority Data

Aug. 4, 2008  (JP) .................................. 2008-201260

(51) Int. Cl.

| | | |
|---|---|---|
| *A61M 25/00* | (2006.01) | |
| *A61M 37/00* | (2006.01) | |
| *A61B 1/018* | (2006.01) | |
| *A61B 17/34* | (2006.01) | |
| *A61B 19/00* | (2006.01) | |
| *A61B 1/267* | (2006.01) | |
| *A61N 5/10* | (2006.01) | |
| *A61B 17/00* | (2006.01) | |

(52) U.S. Cl.
CPC ............ *A61M 37/0069* (2013.01); *A61B 1/018* (2013.01); *A61B 2017/347* (2013.01); *A61B 2019/4857* (2013.01); *A61B 19/54* (2013.01); *A61B 1/2676* (2013.01); *A61N 5/1007* (2013.01); *A61B 2017/0034* (2013.01); *A61B 2019/5487* (2013.01)
USPC .................................. 600/433; 600/1; 604/57

(58) Field of Classification Search
CPC .......... A61B 19/54; A61B 2019/5487; A61M 37/0069
USPC .......... 600/1–8, 424, 431–435; 604/57, 59–64
See application file for complete search history.

(56) References Cited

U.S. PATENT DOCUMENTS

| | | | | |
|---|---|---|---|---|
| 6,530,875 B1 * | 3/2003 | Taylor et al. | ...................... | 600/7 |
| 6,569,077 B2 * | 5/2003 | Schmidt | ........................... | 600/7 |

(Continued)

FOREIGN PATENT DOCUMENTS

| | | |
|---|---|---|
| JP | 2001-120558 | 5/2001 |
| JP | 2003-503098 | 1/2003 |

(Continued)

OTHER PUBLICATIONS

Office Action issued by the Japanese Patent Office on May 22, 2012 in connection with corresponding Japanese Patent Application No. 2008-201260.

(Continued)

*Primary Examiner* — Charles A Marmor, II
*Assistant Examiner* — Carrie R Dorna
(74) *Attorney, Agent, or Firm* — Ostrolenk Faber LLP

(57) ABSTRACT

An endoscopic medical tool is endoscopically inserted into a body cavity in order to eject a member into the body cavity, and includes: a flexible sheath having an inner cavity; an elastically deformable stopper which is provided projecting out toward the inner cavity in a distal end portion of the sheath, and prevents the member which has been loaded inside the sheath from falling out of the sheath; and a pusher which is inserted into the sheath in a freely advancing and retracting manner, and which pushes out and ejects the member from the sheath. In the endoscopic medical tool, the stopper is formed in only a partial region of the inner cavity so that the stopper does not continuously formed over the entire circumference of the inner cavity.

5 Claims, 18 Drawing Sheets

(56) References Cited

U.S. PATENT DOCUMENTS

| | | | |
|---|---|---|---|
| 7,150,709 B1 * | 12/2006 | Schmidt et al. | 600/7 |
| 2005/0080339 A1 * | 4/2005 | Sirimanne et al. | 600/431 |
| 2005/0251111 A1 | 11/2005 | Saito et al. | |
| 2007/0021714 A1 * | 1/2007 | Miller | 604/60 |

FOREIGN PATENT DOCUMENTS

| | | |
|---|---|---|
| JP | 2004-154485 | 6/2004 |
| JP | 3960904 | 5/2007 |
| JP | 2008513043 | 5/2008 |
| WO | WO 01/00101 | 1/2001 |
| WO | WO 2005/122870 | 12/2005 |

OTHER PUBLICATIONS

Translation of Office Action issued by the Japanese Patent Office on May 22, 2012 in connection with corresponding Japanese Patent Application No. 2008-201260.

* cited by examiner

ENDOSCOPIC MEDICAL TOOL AND MEDICAL SYSTEM

BACKGROUND OF THE INVENTION

1. Field of the Invention

The present invention relates to an endoscopic medical tool that is endoscopically inserted into a body cavity and employed for diagnosis and treatment, and a medical system.

Priority is claimed on Japanese Patent Application No. 2008-201260, filed Aug. 4, 2008, the content of which is incorporated herein by reference.

2. Description of Related Art

The number of patients with peripheral lung cancer and the like has been trending upward in recent years. Among such patients, there are an increasing number of cases in which endoscopical diagnosis and treatment is carried out. Cases in which stereotactic radiotherapy is carried out in the treatment of such diseases are also on the rise.

In such stereotactic radiotherapy, in the case where the organ demonstrates a large amount of movement accompanying respiration or the like, particularly as in the case of the lungs, a radiopaque marker is disposed so as to fit into a peripheral bronchial tube near the diseased site, in order to identify and clarify the area to be irradiated. Radiation is then performed on the target tissue white carrying out real-time tracking of the irradiated tissue using the marker as a target.

The medical tool disclosed in Japanese Patent No. 3960904 may be cited as a conventionally known medical tool for disposing the above-described marker. In this medical tool, an radiographic marker member made of a radiopaque material is inserted into a sheath. At the disposition site, the radiographic marker member is pushed from the proximal end side to the distal end side by means of a guide unit. The distal opening of the sheath is formed to have an inner diameter that narrows distally. This distal opening of the sheath is elastically expanded when the radiographic marker member is pushed therein, and the marker is ejected from the distal opening.

SUMMARY OF THE INVENTION

An endoscopic medical tool according an aspect of the present invention is endoscopically inserted into a body cavity in order to eject a member into the body cavity, and includes: a flexible sheath having an inner cavity; an elastically deformable stopper which is provided projecting out toward the inner cavity in a distal end portion of the sheath, and prevents the member which has been loaded inside the sheath from falling out of the sheath; and a pusher which is inserted into the sheath in a freely advancing and retracting manner, and which pushes out and ejects the member from the sheath. In the endoscopic medical tool, the stopper is formed in only a partial region of the inner cavity so that the stopper does not continuously formed over the entire circumference of the inner cavity.

A medical system according an aspect of the present invention is endoscopically inserted into a body cavity in order to eject a member into the body cavity, and includes: the endoscopic medical tool according to claim 1; and a cartridge which has an insertion part capable of inserting into the endoscopic medical tool, and inside which the member is housed.

DETAILED DESCRIPTION OF THE INVENTION

<First Embodiment>

A marker disposing tool (hereinafter referred to simply as "disposing tool") will now be explained with reference to the accompanying FIGS. 1 through 21B as an endoscopic medical tool according to a first embodiment of the present invention.

Figure 1:
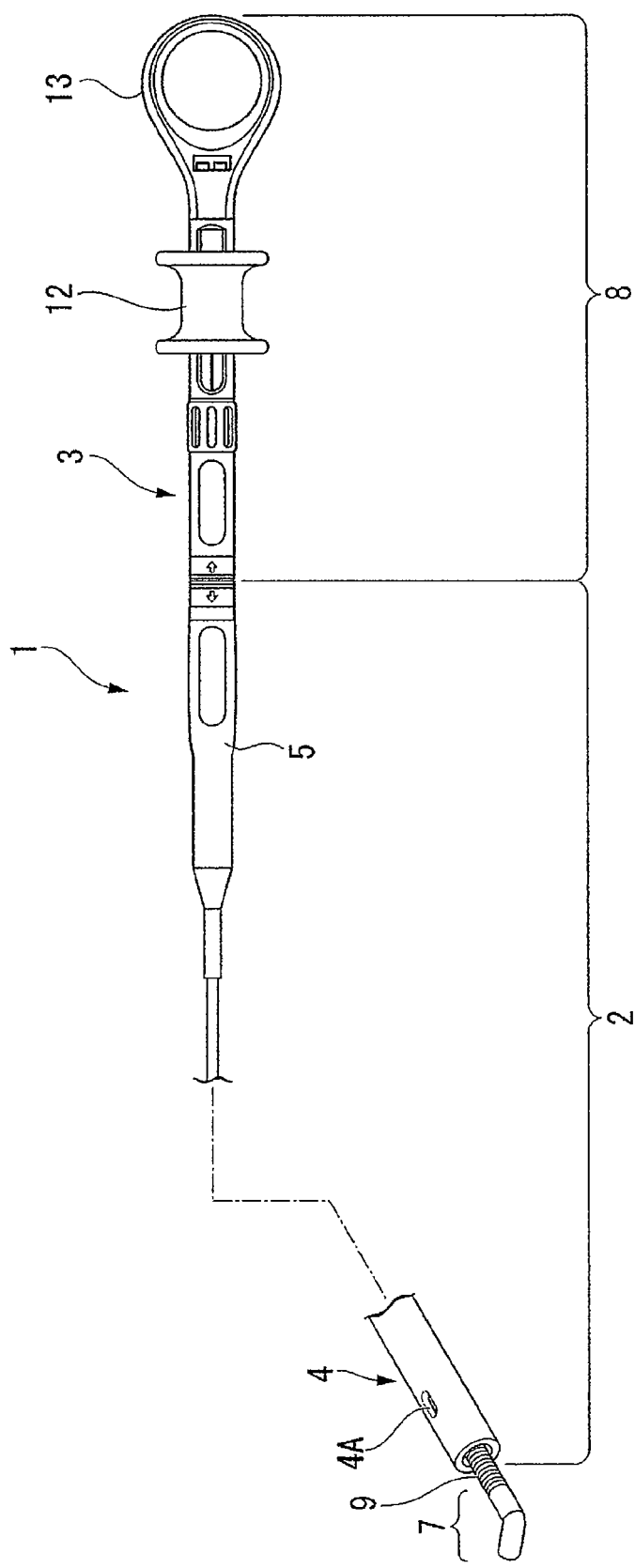
FIG. 1 is an overall view of a marker disposing tool which is an endoscopic medical tool according to a first embodiment of the present invention.

As shown in FIG. 1, the disposing tool 1 according to this embodiment includes an outer cannula 2 and a guide unit (pusher) 3. The guide unit 3 is inserted into the outer cannula 2, and is assembled in a freely advancing and retracting, and attaching and releasing, manner. In this assembled state, the tool 1 is inserted into the body cavity of the patient or the like via an endoscope such as a bronchoscope.

Figure 3:
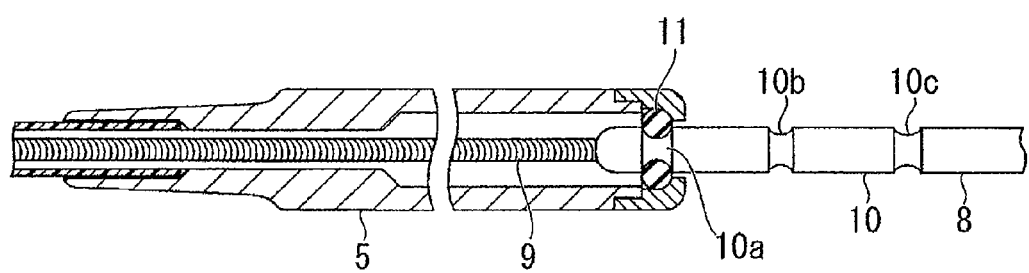
FIG. 3 is a cross-sectional view of a proximal end of an outer cannula of the same marker disposing tool.

The outer cannula 2 is provided with a long sheath 4 as its main body, this long sheath having flexibility sufficient to permit insertion into an instrument channel of the endoscope, and with a connector 5 which is provided to the proximal end side of the sheath 4. The connector 5 is mechanically connected to the proximal end portion of the sheath 4 as shown in FIG. 3. The inner cavity of the sheath 4 and the inner cavity of the connector 5 mutually communicate.

Figure 2:
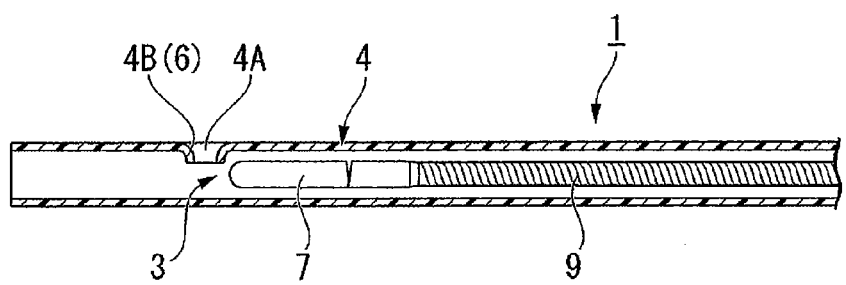
FIG. 2 is a cross-sectional view of a distal end portion of the same marker disposing tool.

A hole 4A communicating with the inner cavity is formed to the distal end side of the sheath 4 of the outer cannula 2. A wall surface (outer surface) 4B of the sheath 4 which is positioned around the hole 4A projects out so as to drop into the inner cavity as shown in FIG. 2. This wall surface 4B functions as a stopper 6 for reliably housing a marker (described later) inside the sheath 4. In order for the wall surface 4B to function as a stopper, the projecting length is adjusted so that the inner diameter at the maximally projected portion on the inner cavity side of the wall surface 4B is less than the outer diameter of the marker to the disposed.

Note that when the sheath 4 is formed out of a fluorinated material such as polytetrafluoroethylene (PTFE), the fibrous structure that this material possesses makes it possible for the wall surface 4B to naturally bend toward the inner cavity side simply by forming the hole 4A by passing a needle or the like from the outer surface into the inner cavity. A stopper 6 can be easily formed as a result.

The guide unit 3 is formed by mechanically connecting a distal working part 7 and an operator part 8, which operates this distal working part 7, via a metallic sheath 9 made of a long coil or the like.

As shown in FIG. 3, the sheath 9 and the operator part 8 of the guide unit 3 are joined by connecting the sheath 9 to the distal end of a slider rod 10 which is formed extending in the forward direction from the operator part 8.

A plurality of engaging grooves 10a, 10b, 10c are formed at specific spacing intervals along the slider rod 10. These engaging grooves 10a, 10b, 10c engage with a convex member 11 that is attached inside the connector 5 of the outer cannula 2, projecting toward the inner cavity side, respectively. As a result, the guide unit 3 is stopped and fixed in place at a specific position with respect to the outer cannula 2.

The convex member 11 is formed in the shape of a ring from an elastic material or the like, and can slidably move with respect to the slider rod 10, and can engage in a freely attaching and releasing manner with the engaging grooves 10; 10b, 10c. Accordingly, by pulling or pushing the entirety of the operator part 8, one of the engaging grooves 10a, 10b, 10c engages with the convex member 11 which is provided inside the outer cannula 2. As a result, it is possible to form a so-called three-step click mechanism in which the stopping position of the guide unit 3 with respect to the outer cannula 2 can be selected from among a first position, a second position or a third position.

In other words, at the stopping position shown in FIG. 3, the convex member 11 engages with the first engaging groove 10a. At this time, the distal working part 7 at the distal end of the guide unit 3 is housed inside the sheath 4 of the outer cannula 2 as shown in FIG. 2. In this housed state, the distal working part 7 of the guide unit 3 is restricted by the inner wall of the sheath 4, so that it lies straight state along the sheath 4.

Figure 4:
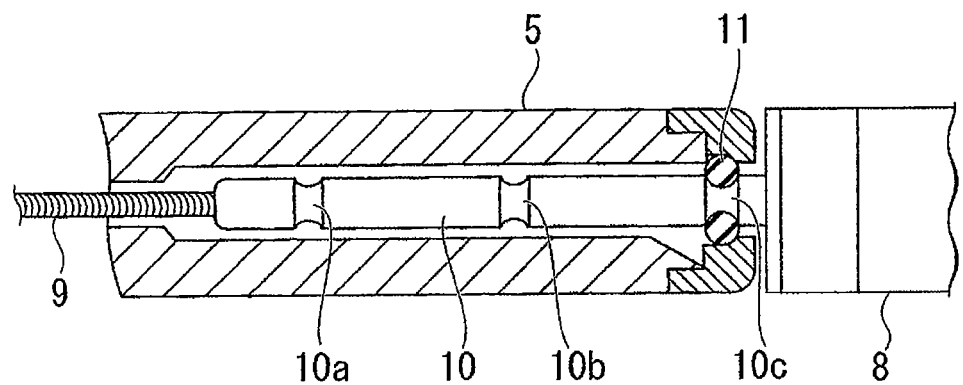
FIG. 4 is a cross-sectional view of the proximal end of the same outer cannula.
Figure 5:
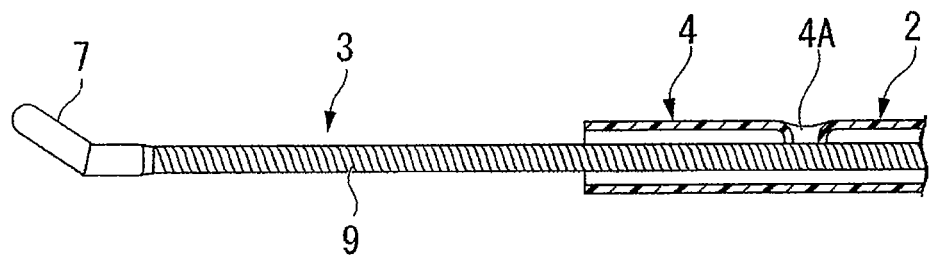
FIG. 5 is a view showing a distal end side of the same marker disposing tool when the proximal end of the outer cannula is in the arrangement shown in FIG. 4.
Figure 6:
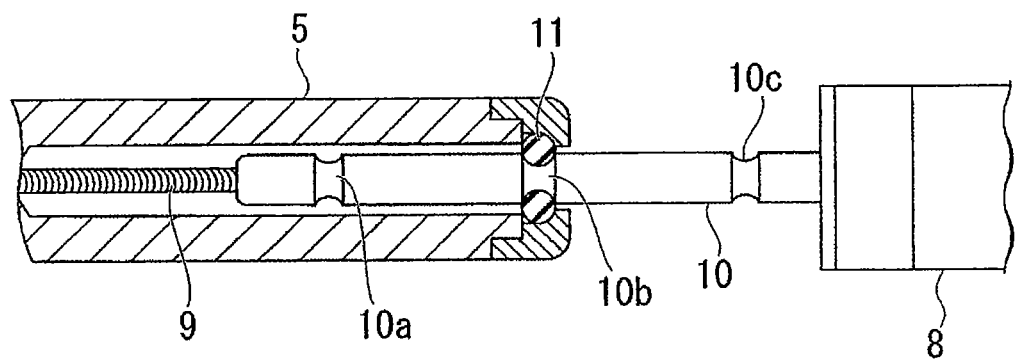
FIG. 6 is a cross-sectional view of the proximal end of the same outer cannula.
Figure 7:
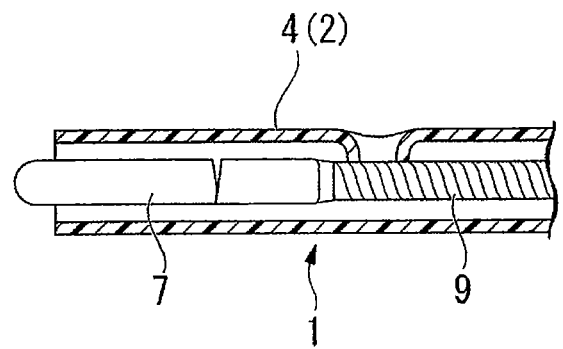
FIG. 7 is a view showing the distal end side of the same marker disposing tool when the proximal end of the outer cannula is in the arrangement shown in FIG. 6.

Further, when the convex member 11 is in the stopped state in which it is engaged with the engaging groove 10c which is positioned closest to the hand held side, as shown in FIG. 4, the distal working part 7 at the distal end of the guide unit 3 is completely projected out from the distal end of the sheath 4, as shown in FIG. 5. Further, when the convex member 11 in the stopped state in which it is engaged with the engaging groove 10b which is positioned in the middle, as shown in FIG. 6, only a portion of the distal working part 7 projects out slightly from the sheath 4, as shown in FIG. 7.

As explained above, parameters such as the length of the guide unit 3, the distance between the various engaging grooves 10a, 10b, 10c, and the like, are set so that the stopping position defined by the connector 5 and the engaging grooves, and the relative positional relationship between the distal working part 7 and the distal end of the sheath have the relationships as shown in FIGS. 3 through 7. Note that in this embodiment, three engaging grooves are installed with an equal spacing interval, however, the number and installation position of the engaging grooves can be suitably varied within the range of the length of the slider rod 10.

Figure 8:
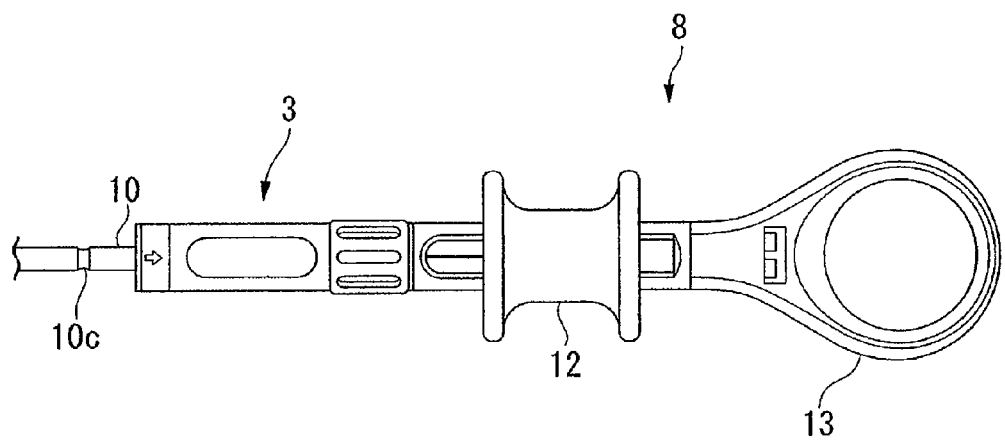
FIG. 8 is a view showing an operator part of a guide unit of the same marker disposing tool.

As shown in FIG. 8, a slider 12 and a finger ring 13 are provided in the operator part 8 of the guide unit 3. The proximal end of an operating wire 14 (described later) is connected to the slider 12. This operating wire 14 is passed through the inside of the sheath 9 and the slider rod 10, and is guided to the distal end. The distal end of the operating wire 14 is connected to the moving member of the distal working part 7 of the guide unit 3.

Figure 9:
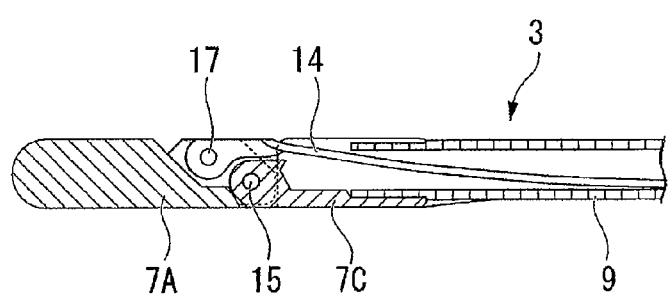
FIG. 9 is a view showing an arrangement in which the distal end of the guide unit is curved.

As shown in FIG. 9, the distal working part 7 of the guide unit 3 is formed by connecting a distal end 7A, which has a spherical distal end portion, and a proximal end portion 7C in a linear array. The proximal end 7C and the distal end 7A are connected via a pivot pin 15.

The position of the pivot pin 15, which pivotally attaches the distal end 7A and the proximal end 7C, is disposed so as to be inclined with respect to the center of the distal working part 7. For this reason, the proximal end 7C and the distal end 7A of the distal working part 7 are formed as a bending part which can bend upward in FIG. 9.

Note that it is also acceptable to connect the distal end 7A and the proximal end 7C with a deformable thin part, rather than with a pivot pin 15.

The operating wire 14 passes from the sheath 9 through the base part 7C, to the distal end 7A, with the distal end of the operating wire 14 connecting to the distal end 7A. Specifically, a wire connecting pin 17 is provided to the distal end 7A, substantially parallel to the width direction of the distal end 7A. The distal end 7A and the operating wire 14 are connected to each other by inserting the wire connecting pin 17 into the annularly-shaped distal end portion of the operating wire 14.

In addition, a bending operating means is formed in which the distal working part 7 is bent by advancing or retracting the operator part wire 14 through push/pull operation of the slider 12 of the operator part 8.

In other words, when the slider 12 is pulled toward the proximal end side, and the distal end 7A of the distal working part 7 is pulled by the operating wire 14 as shown in FIG. 9, the distal end 7A rotates centered on the pivot pin 15 with respect to the proximal end 7C, causing bending of the distal working part 7. The degree of curving (bending) can be optionally adjusted according to the distance that the slider 12 is moved.

An explanation will now be made of the actions when disposing a radiographic marker using the disposing tool 1 designed as described above, at or near a diseased site in a bronchial tube in which an endoscope cannot reach.

First, the user confirms the position of a target tissue such as a diseased site using a radiotransparent object and the like, and advances a distal end of a bronchoscope inside the bronchial tube toward the target tissue, to a position which permits insertion of the distal end of the bronchoscope.

Figure 10:
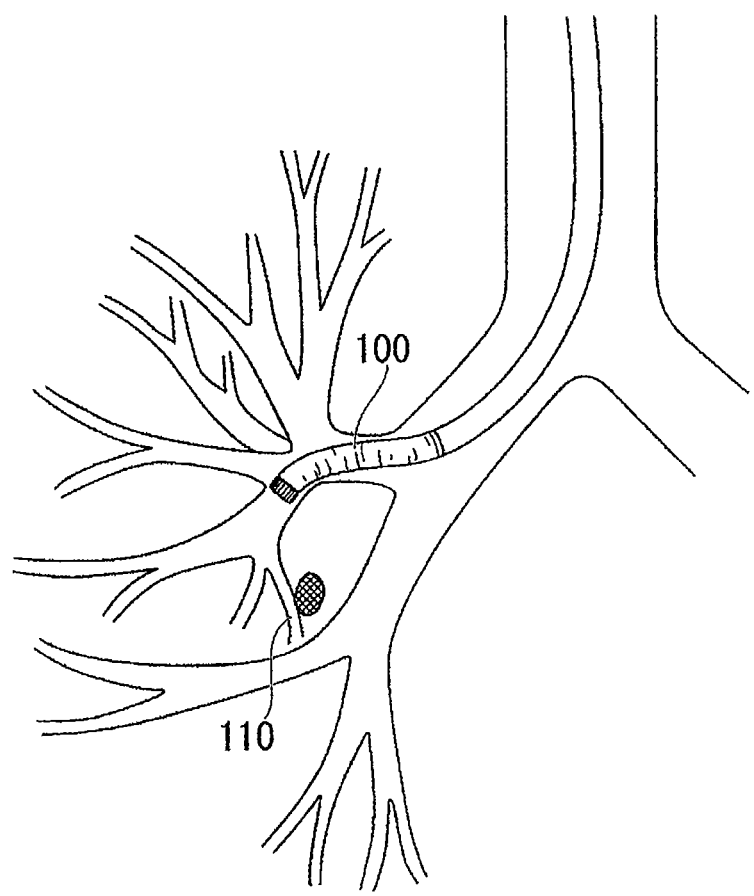
FIG. 10 is a view showing the action when the same marker disposing tool is used inside the lung.
Figure 11:
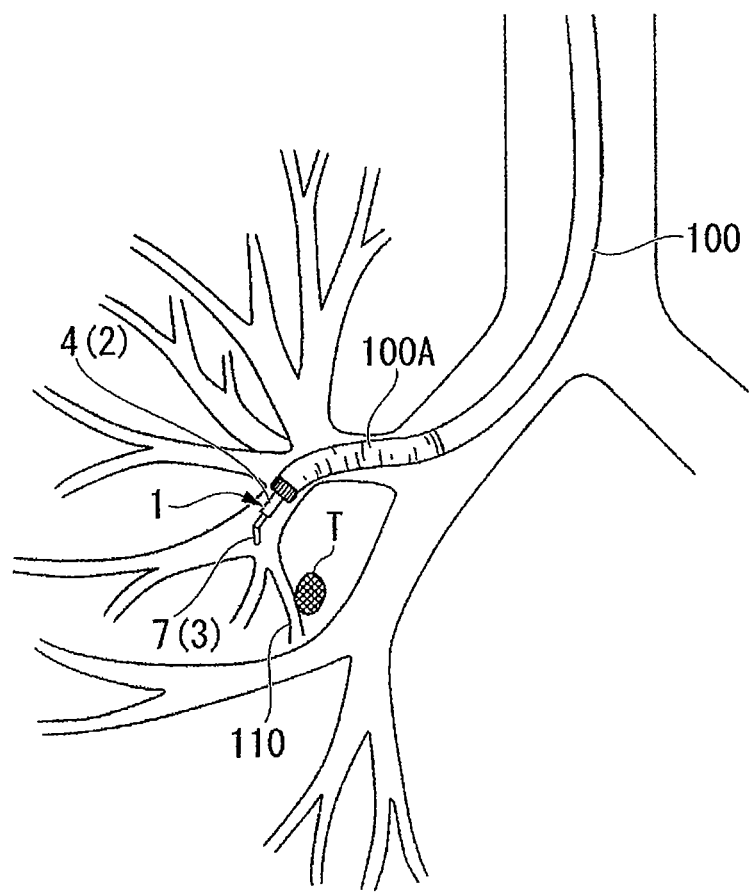
FIG. 11 is a view showing the action when the same marker disposing tool is used inside the lung.

As shown in FIG. 10, the distal end of the bronchoscope 100 is moved near the front of a bronchiole 110 which has an inner diameter that is too small to permit insertion of the distal end of the bronchoscope 100. At this point, the user inserts the disposing tool 1 via a forceps opening (not shown in the figures) in bronchoscope 100 into the instrument channel of the bronchoscope 100, and projects the distal end of the disposing tool 1 out from the distal end of the bronchoscope 100, as shown in FIG. 11. Note that it is also acceptable to insert the disposing tool 1 into the instrument channel prior to insertion of the bronchoscope 100 into the body cavity.

Next, the user advances the disposing tool 1 into the bronchiole 110 using radioscopy, so that it approaches the target tissue T.

The user then suitably curves (bends) the distal working part 7 while pushing/pulling the slider 12 at the operator part 8 of the guide unit 3, selects the bronchiole 110 into which the bronchoscope should be inserted, and advances the distal working part 7 thereto. It is also acceptable to carry out the approach of medical tool 1 by suitably combining the bending manipulation of the bending part 100A of the bronchoscope 100.

Figure 12:
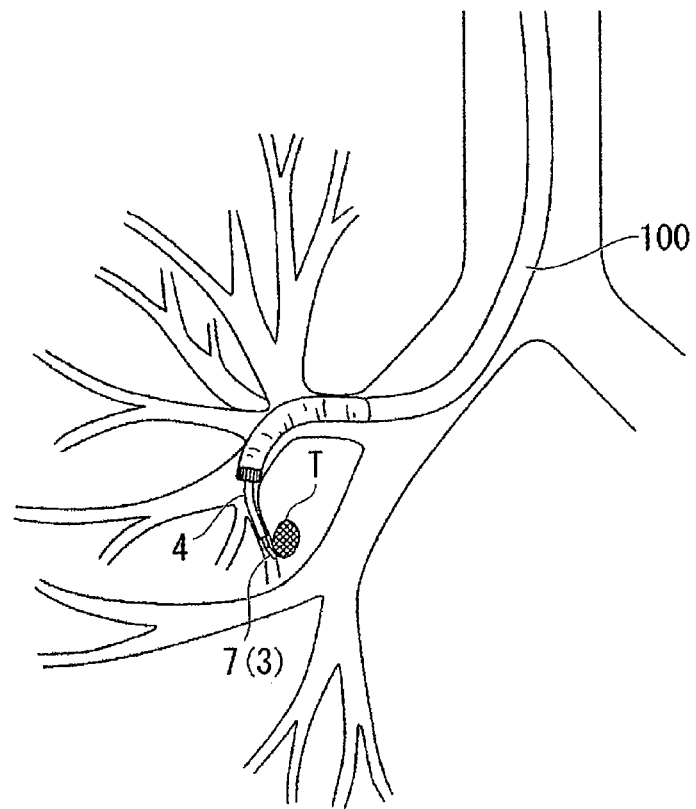
FIG. 12 is a view showing the action when the same marker disposing tool is used inside the lung.

As shown in FIG. 12, once the distal working part 7 at the distal end of the guide unit 3 reaches the marker disposition site near the target tissue T, the user once withdraws the guide unit 3 from the endoscope while leaving the distal end of the sheath 4 near the marker disposition site. A known spherical marker employed for disposition within the body, made of a radiopaque material, is loaded from the connector 5 side at the proximal end of the sheath 4 into the inner cavity of the outer cannula 2, and the guide unit 3 is once again inserted into the sheath 4.

Figure 13A:
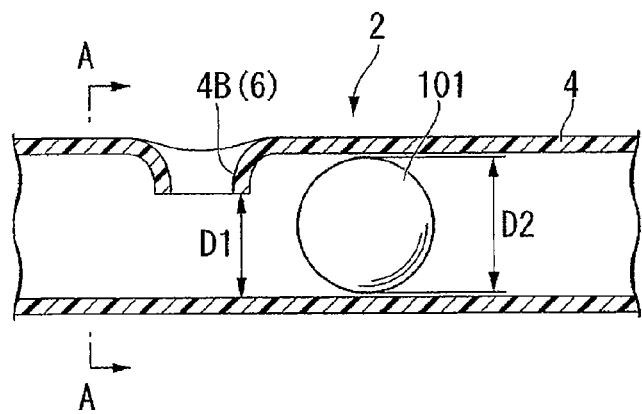
FIG. 13A is a view showing an arrangement in which a marker is loaded in the same marker disposing tool.
Figure 13B:
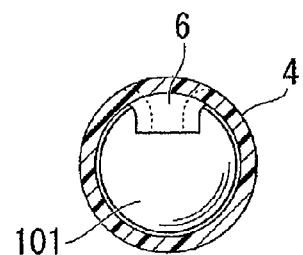
FIG. 13B is a cross-sectional view along the line A-A in FIG. 13A.
Figure 14:
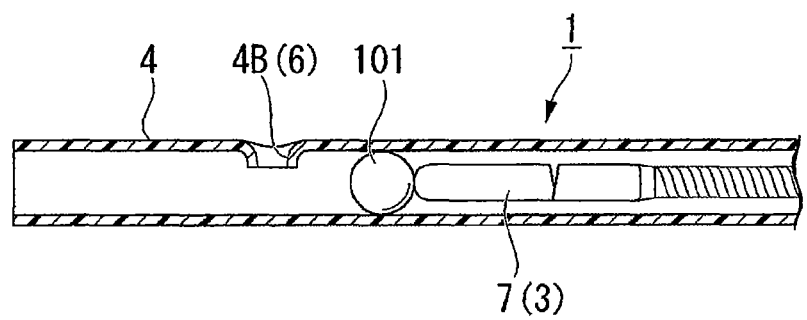
FIG. 14 is a view showing the action when ejecting the same marker.

FIG. 13A is a view showing the spherical marker 101 used for disposition inside the body (hereinafter referred to simply as "marker") which is a member loaded inside the sheath 4. FIG. 13B is a cross-sectional view along the line A-A in FIG. 13A. The marker 101 which has been loaded in the outer cannula 2 is advanced by the inserted guide unit 3 so as to be pushed toward the distal end side of the sheath 4 as shown in FIG. 14. However, since the stopper 6 which is formed from the projection of the wall surface 4B toward the inner cavity is present near the distal end of the sheath 4, a portion of the marker 101 comes into contact with the stopper 6 and comes to a halt. As a result, the marker 101 is prevented from falling out of the sheath 4 at an unintentional timing during the procedure.

In this embodiment, the minimal dimension D1 (see FIG. 13A) in the radial direction of the inner cavity of the sheath 4 at the position where the stopper 6 is provided is 1.0 millimeters (mm). The outer diameter of the marker 101 is set to be 1.5 mm. While this is just an example, in this case, a comparatively large difference of approximately 0.5 mm relative to the outer diameter of the marker 101 is formed by the stopper 6 in the inner cavity of the sheath 4.

Figure 15:
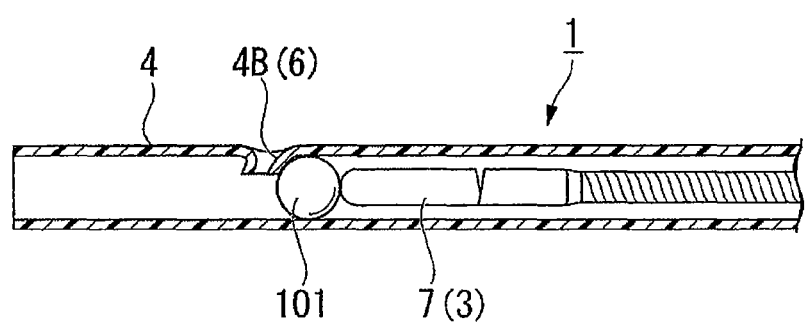
FIG. 15 is a view showing the action when ejecting the same marker.
Figure 16:
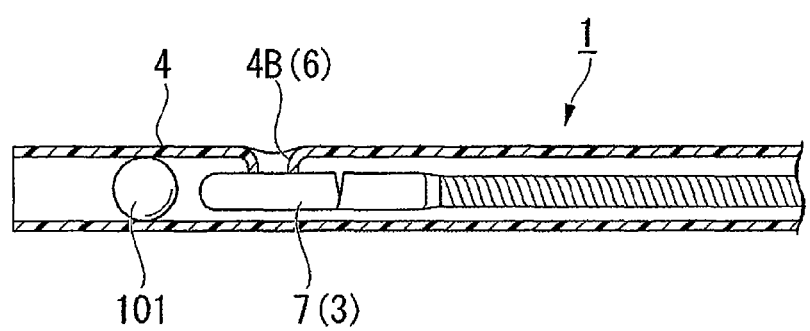
FIG. 16 is a view showing the action when ejecting the same marker.

After the marker 101 has been temporary stopped within the sheath 4 by the stopper 6, the user further pushes the guide unit so as to advance it with respect to the outer cannula 2, in order to dispose the marker 101. The marker 101 causes an elastic deformation of the wall surface 4B of the stopper 6 as shown in FIG. 15 as a result, so that it rides over the stopper 6 as shown in FIG. 16 and moves farther toward the distal end side of the sheath 4.

Figure 17:
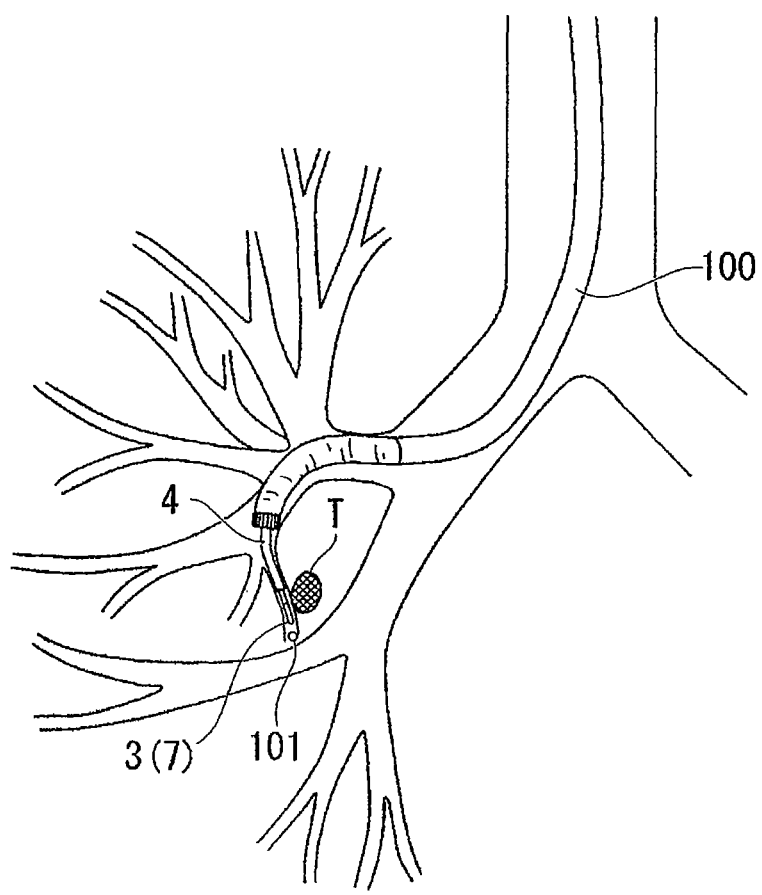
FIG. 17 is a view showing the action when the same marker disposing tool is used inside the lung.
Figure 18A:
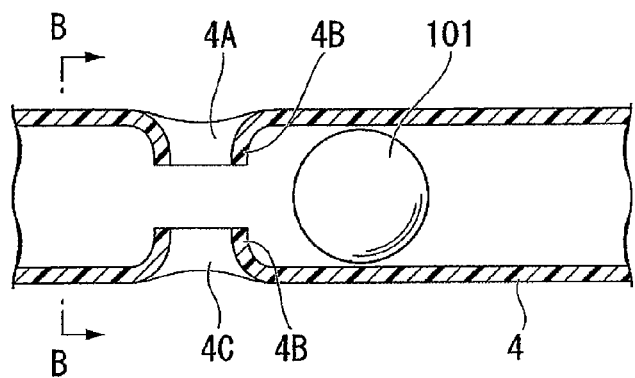
FIG. 18A is a view showing an arrangement in which the marker is loaded in a marker disposing tool according to a modification of the first embodiment.
Figure 18B:
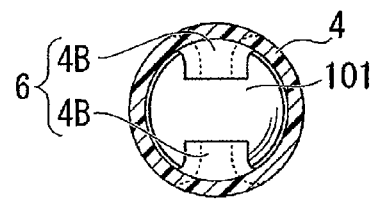
FIG. 18B is a cross-sectional view along the line B-B in FIG. 18A.

When the user further pushes the guide unit 3, the marker 101 is ejected from the distal end of the sheath 4 as shown in FIG. 17, and is disposed at the placement site. The user confirms the ejection via radioscopy while at the same time also gaining confirmation from the click sensation that is generated by engagement of the slider rod 10 with the convex member 11.

After the marker 101 has been disposed, the user suitably changes the bronchiole into which the medical tool 1 is to be inserted and repeats the above actions. The required number of markers is thus disposed around the treatment target tissue T. Then, using the disposed markers as indicators, a conventional device is employed to carry out various procedures such as radiation on the target tissue T.

In the medical tool 1 according to the present embodiment, the stopper 6 formed of the side wall 4B comes into contact with only the portion of the marker 101 that is positioned on the inner wall side of the sheath 4. As a result, the marker 101 can be prevented from falling out of the sheath 4 at an unintentional timing.

Accordingly, by employing a method such as constricting the diameter of the distal end side of the sheath 4, it is possible to markedly reduce the amount of force necessary to push out the guide unit 3 when ejecting the marker 101, as compared to the case where there is contact with the entire region of a marker 101 that is positioned on the inner wall side of the sheath 4. As a result, the disposition operation is made easy, and it is possible to control the distal end of the guide unit with greater certainty during ejection.

Further, since it is possible to reduce the amount of push out force required during ejection of the marker 101 as described above, it is possible to increase the length of projection of the stopper 6 into the inner cavity of sheath 4 so that it is a relatively larger proportion of 20~30% with respect to the diameter of the marker. As a result, it is possible to more certainly prevent the marker from falling out, while still maintaining the ease of ejection and disposition.

In this embodiment, an example was explained in which the stopper 6 is provided to a single site only. However, in place thereof, it is also acceptable to design a stopper 6 by additionally forming a hole 4C at a position roughly opposite the hole 4A to form side walls 4B that project into the inner cavity side of the sheath 4 at two sites, such as in the modification shown in FIGS. 18A and 18B.

Figure 19A:
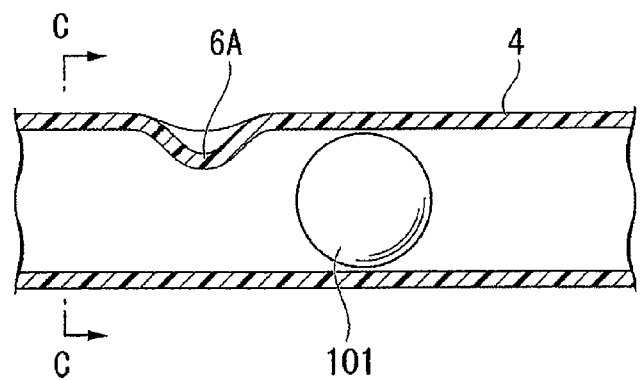
FIG. 19A is a view showing an arrangement in which the marker is loaded in a marker disposing tool according to a modification of this embodiment.
Figure 19B:
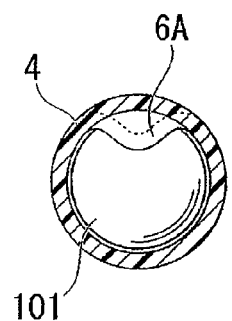
FIG. 19B is a cross-sectional view along the line C-C in FIG. 19A.

Further, in place of providing a stopper by forming a hole as in the present embodiment, it is also acceptable to design a stopper 6A in which a portion of the inner wall of the sheath 4 is made to project out toward the inner cavity side, as a dent, formed by bending an approximately circular part of a side wall of the sheath in a direction approximately perpendicular to the longitudinal direction of the sheath, wherein the dent projects in toward the inner cavity by deforming part of the sheath 4 using a method such as thermoforming, such as in the modification shown in FIGS. 19A and 19B.

Note that in either of these cases, the amount of force required for pushing out the guide unit during ejection can be adjusted to a desired value by suitably adjusting the number and position of the structure(s) that project out toward the inner cavity.

The sheath 9 in this embodiment may be a so-called multi-wire coil into which a plurality of wires are wound. In this embodiment, the distal working part 7 is moved to the marker disposition site while pushing/pulling the slider 12 at the operator part 8 to arbitrarily bend the distal working part 7. When changing the bending direction of the distal working part 7, the distal working part 7 is rotated via the sheath 9 by rotating the operator part 8. When the sheath 9 is formed of the multi wire coil with high torque transmissibility, it is possible to improve the rotation following capability of the sheath 9. This makes it easier to adjust the bending direction of the distal working part 7.

<Second Embodiment>

Next, a second embodiment of the present invention will be explained with reference to FIGS. 20A through 21B. The point of difference between the medical tool according to this embodiment and the medical tool 1 of the first embodiment described above is that the stopper is formed in the distal end of the sheath.

Note that the same numerical symbol will be applied to structures that are in common with the first embodiment and a redundant explanation thereof will be omitted.

Figure 20A:
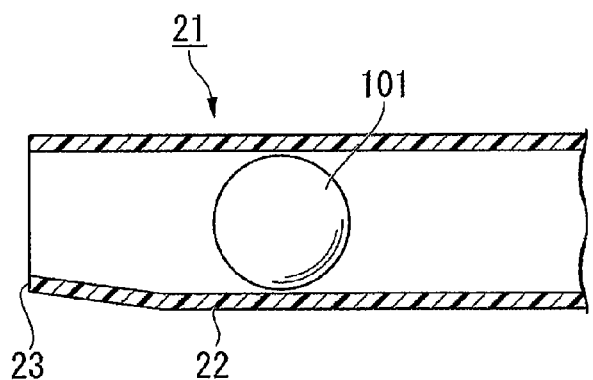
FIG. 20A is a cross-sectional view of a distal end portion of a marker disposing tool according to a second embodiment of the present invention.
Figure 20B:
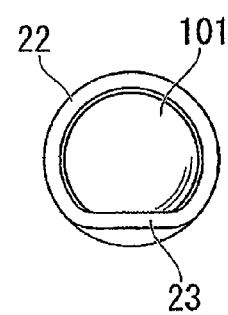
FIG. 20B is a view of the same marker disposing tool as seen from the distal end side.

FIG. 20A is a cross-sectional view along the axial direction near a distal end of a sheath 22 of a medical tool 21 according to the present embodiment. FIG. 20B is a view of the sheath 22 as seen from the distal end side. A portion of the distal end of the sheath 22 forms a linear part 23 in which the portion has a linear form as a result of thermoforming or the like.

In other words, as shown in FIG. 20B, the sheath 22 has a roughly D-shaped inner cavity at its distal end that includes the linear part 23. In addition, the inner wall of the sheath 22 at the linear part 23 projects out farther toward the inner cavity side than the inner wall at the position where the cross-section thereof is circular, closer to the proximal end. As a result, this portion of the inner wall functions as a stopper for preventing the marker 101 from falling out of the sheath 22.

The medical tool 21 according to this embodiment provides the same effects as those of the medical tool 1 according to the first embodiment.

Further, since the linear part 23 which functions as a stopper is provided to the distal end of the sheath 22, the marker 101 which is loaded inside the sheath 22 can be housed inside the sheath 4 at a position which is closer to the distal end thereof. Accordingly, it is possible to reduce the amount that the guide unit 3 is moved (i.e., the amount that the guide unit 3 is pushed out) along the axial direction when ejecting the marker 101, and to more certainly control the behavior of the distal end of the guide unit. As a result, a procedure can be carried out safely even at a location requiring a serious procedure, such as near the periphery of a bronchiole.

In this embodiment, an example was explained in which a stopper was provided by forming the distal end of the sheath in the D-shape, which has the linear part. However, the shape of the distal end of the sheath for the provision of the stopper is not limited thereto.

Figure 21A:
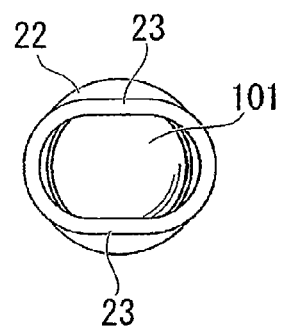
FIGS. 21A and 21B are both views showing a marker disposing tool according to a modification of the second embodiment as seen from the distal end side.
Figure 21B:
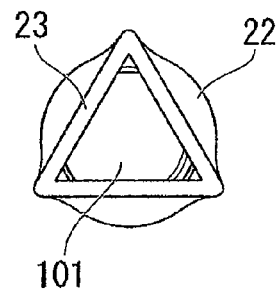

For example, it is acceptable to form the distal end of the sheath 22 to be approximately oval, in which there are linear parts 23 at two sites, as in the modification shown in FIG. 21A, or to provide a stopper at the distal end of the sheath by forming the distal end of the sheath 22 with a triangular or other polygonal shape having only linear parts 23, as in the modification shown in FIG. 21B.

In addition, it is also acceptable to provide a stopper at the distal end of the sheath by forming a structure which is not linear but projects out toward the inner cavity, such as the stopper 6A shown in FIG. 19A.

It is also acceptable to form the stopper by deforming a portion within the sheath by disposing an elastic member of a specific shape inside the sheath, rather than employing the above-described thermoforming.

However, as the surface area over which the marker 101 and the stopper are in contact increases, the amount of push out force that must be applied to the guide unit to cause ejection increases. Accordingly, it is desirable to take this into consideration when designing the shape of the stopper.

<Third Embodiment>

Next, a third embodiment of the present invention will be explained with reference to FIGS. 22 through 28. The point of difference between this embodiment and the first and second embodiments is that a cartridge is used for loading a marker into the sheath 4. Note that the same numerical symbol will be applied to structures that are in common with the first and second embodiments and redundant explanations thereof will be omitted.

Figure 22:
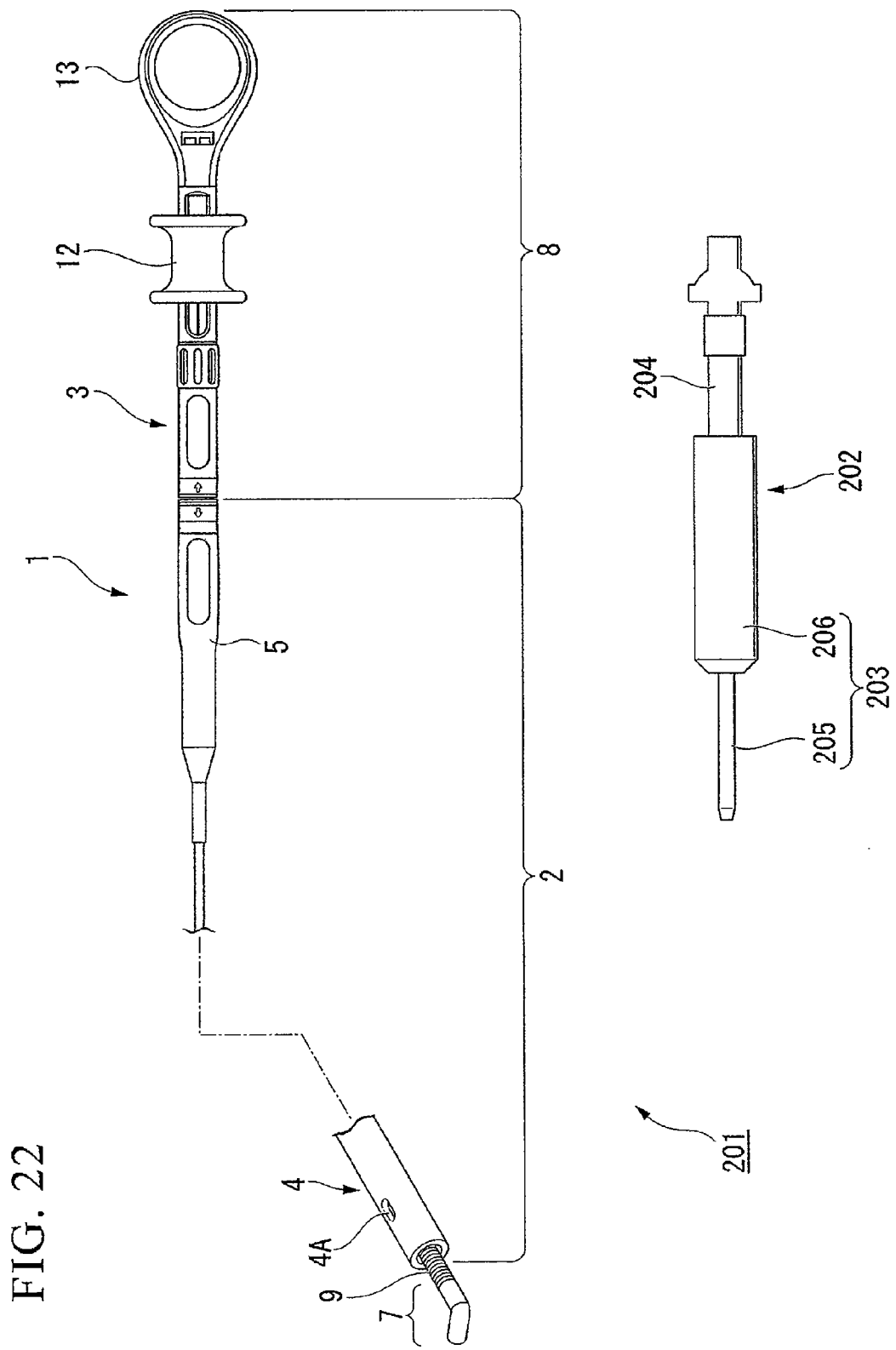
FIG. 22 is an overall view of a medical system for disposing a marker according to a third embodiment of the present invention.
Figure 23:
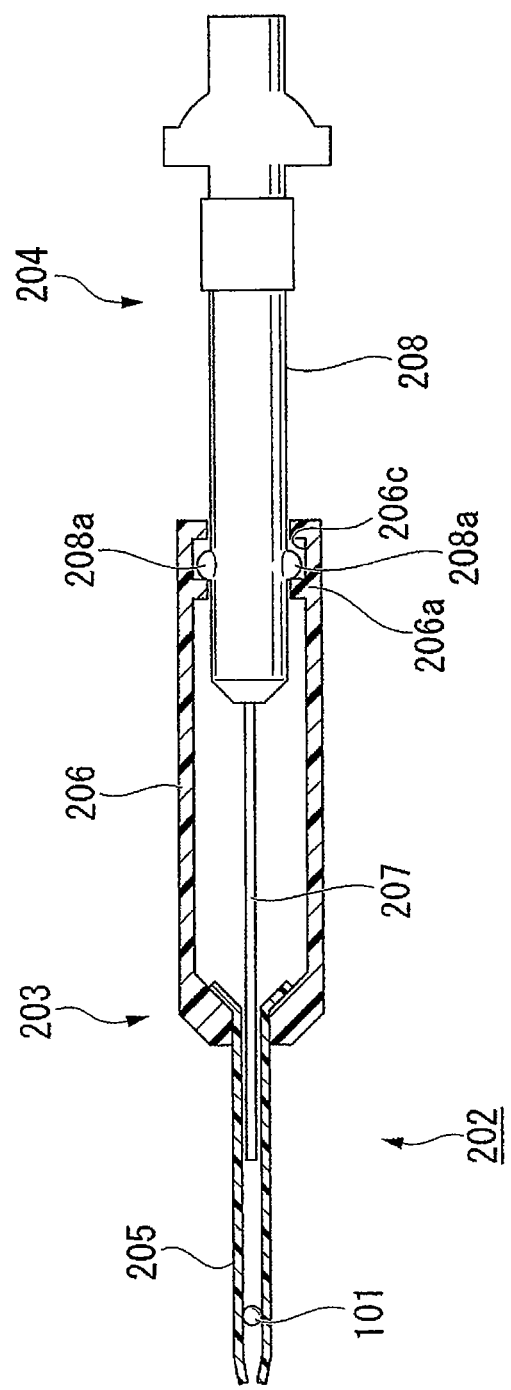
FIG. 23 is a cross-sectional view of a cartridge of the same medical system for disposing a marker.

As shown in FIGS. 22 and 23, a medical system 201 for disposing a marker (hereinafter referred to simply as "medical system") according to this embodiment includes the marker disposing tool 1 according to the first embodiment and a cartridge 202.

The cartridge 202 includes a housing 203 in which the marker 101 is housed, and a pushing part 204 which is inserted into the housing 203 and used for ejecting the marker 101 from the housing 203.

Figure 24:
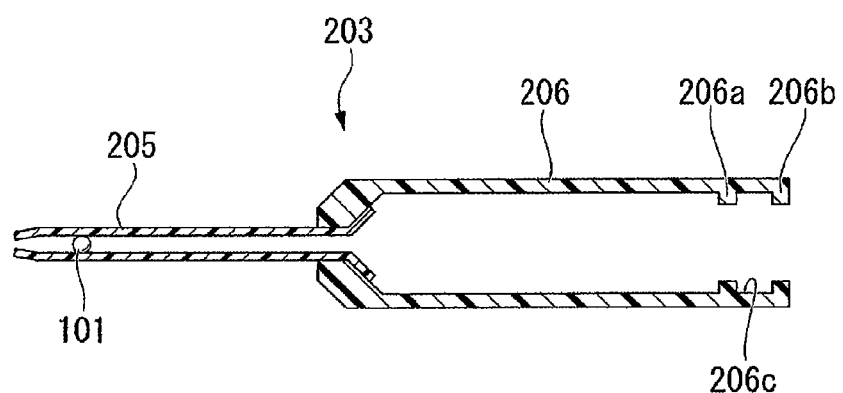
FIG. 24 is a cross-sectional view of a housing of the same cartridge.

As shown in FIG. 24, the housing 203 includes an insertion part 205 which has sufficient flexibility to permit insertion into the sheath 4 of the marker disposing tool 1, and a base portion 206 which is connected to the proximal end of the insertion part 205 and through which the pushing part 204 is inserted. The inner cavity of the insertion part 205 and the inner cavity of the base portion 206 mutually communicate.

The marker 101 is housed inside the insertion part 205 in advance. A distal end portion of the insertion part 205 is formed in a tapered-shape whose inner diameter narrows toward the distal end so that the inner diameter at the distal end of the insertion part 205 is smaller than the outer diameter of the marker 101. First and second projecting portions 206a and 206b are formed on an inner surface of a proximal end portion of the base portion 206 so as to be separated from each other at a specific interval in the axial direction of the base portion 206. An engagement groove 206c is formed between the projecting portions 206a and 206b.

Figure 25:
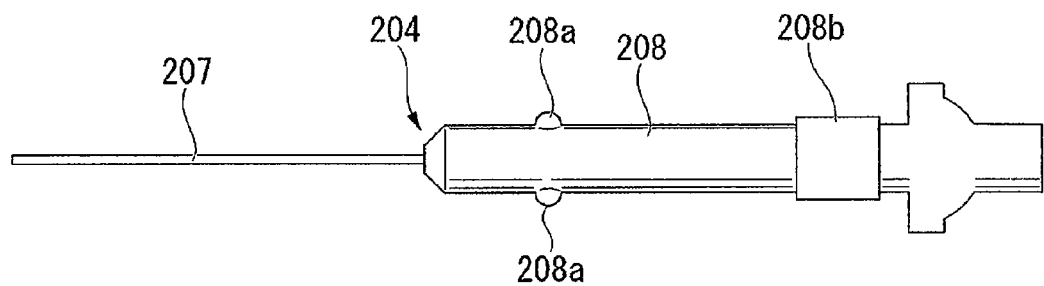
FIG. 25 is a cross-sectional view of a pushing part of the same cartridge.

As shown in FIG. 25, the pushing part 204 includes a rod-shaped cartridge pusher 207 which is inserted into the insertion part 205, and an operator part 208 which is connected to the proximal end of the cartridge pusher 207.

Two elastically deformable protrusions 208a each of which has a semispherical shape are formed on an outer surface of a distal end portion of the operator part 208 so as to oppose each other in a symmetric manner with respect to the axis of the operator part 208. The semispherical-shaped protrusions 208a can engage with the engagement groove 206c in a freely attaching and releasing manner. As shown in FIG. 23, the semispherical-shaped protrusions 208a are engaged with the engagement groove 206 in a state before using the cartridge 202 (hereinafter referred to as "initial state"). In the initial state, the cartridge pusher 207 is slightly inserted into the insertion part 205. Since the semispherical-shaped protrusions 208*a* are engaged with the engagement groove 206, it is possible to prevent the pushing part 204 from moving with respect to the housing 203 at the time of transport. Accordingly, it is possible to prevent the marker 101 from being pushed out from the distal end of the insertion part 205 due to an accidental advance of the cartridge pusher 207. Furthermore, since the cartridge pusher 207 is slightly inserted into the insertion part 205, it is possible to prevent the marker 101 from entering the base portion 206 from the insertion part 205 at the time of transport.

Figure 26:
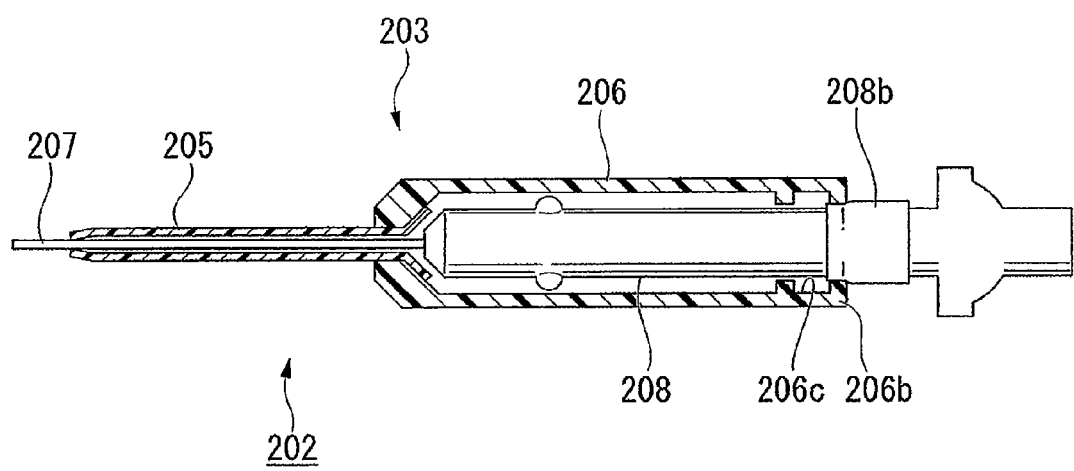
FIG. 26 is a cross-sectional view of the same cartridge when the ejection of a marker has been completed.

An elastically deformable enlarged-diameter portion 208*b* is formed on the outer surface of a proximal end portion of the operator part 208 so as to protrude outwardly in the radial direction. As shown in FIG. 26, when a distal end portion of the enlarged-diameter portion 208*b* is pressed in the inside of the projecting portion 206*b*, the cartridge pusher 207 is completely projected out from the distal end of the insertion part 205.

An explanation will now be made of the actions when disposing a marker using the medical system 201 designed as described above, at or near a diseased site in a bronchial tube.

The user operates the marker disposing tool 1 to advance the guide unit 3 to a marker disposition site near a target tissue T in a state where the guide unit 3 is inserted through the sheath 4. A way of advancing the guide unit 3 is in the same manner as the first embodiment, and an explanation thereof will be omitted here. Then, the user withdraws the guide unit 3 from the endoscope while leaving the distal end of the sheath 4 near the marker disposition site.

Figure 27:
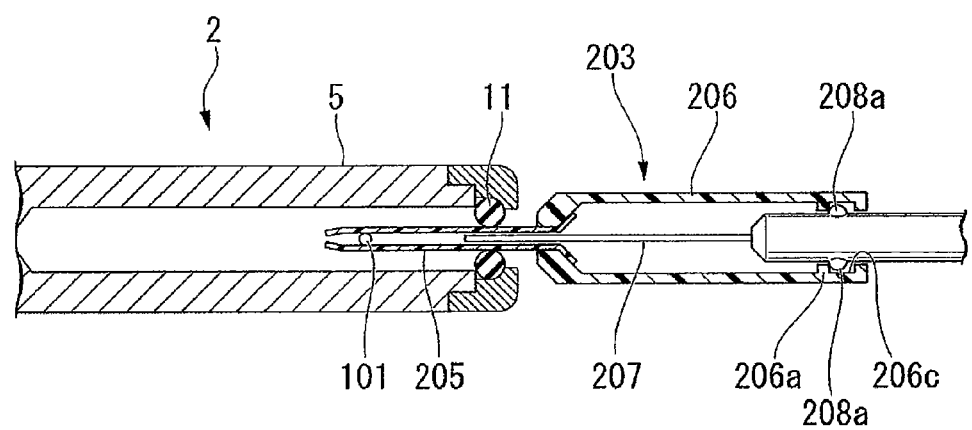
FIG. 27 is a view showing the action of the same medical system for disposing a marker when ejecting the marker.

Next, as shown in FIG. 27, the user inserts the insertion part 205 of the cartridge 202, inside which the marker 101 was housed in advance, into the connector 5 of the outer cannula 2 from the proximal end side. At this time, the cartridge 202 is in the initial state as shown in FIG. 23 such that the semispherical-shaped protrusions 208*a* are engaged with the engagement groove 206*c*. As a result, the pushing part 204 is prevented from advancing with respect to the housing 203, thereby enabling to prevent the marker 101 from being pushed out from the insertion part 205 due to an accidental advance of the cartridge pusher 207. Furthermore, since the distal end portion of the insertion part 205 has a tapered-shape whose inner diameter narrows toward the distal end, it is possible to prevent the marker 101 from falling out of the insertion part 205 at an unintentional timing during the procedure.

Figure 28:
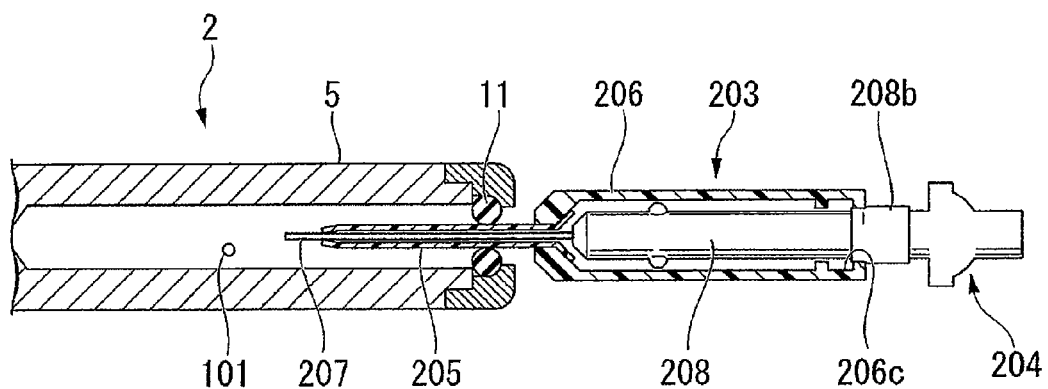
FIG. 28 is a view showing the action of the same medical system for disposing a marker when ejecting the marker.

Next, the user pushes the operator part 208 toward the distal end side. Since the semispherical-shaped protrusion 208*a* is elastically deformable, the engagement of the semispherical-shaped protrusion 208*a* with the engagement groove 206*c* is released and the semispherical-shaped protrusion 208*a* passes over the first projecting portion 206*a*. When further pushing the operator part 208 toward the distal end side, the operator part 208 and the cartridge pusher 207 move forward with respect to the housing 203. The marker 101 is pushed toward the distal end side by the cartridge pusher 207 and is temporary stopped when the marker 101 comes into contact with the taper-shaped distal end portion of the insertion portion 205. When further pushing the operator part 208 toward the distal end side, the pushed marker 101 pushes and spreads the distal end portion of the insertion part 205 having flexibility so that the marker 101 passes through the distal end portion of the insertion part 205. As a result, the marker 101 is ejected from the insertion part 205 as shown in FIG. 28. Since the insertion part 205 is inserted into the connector 5 of the outer cannula 2, the ejected marker 101 passes through the connector 5 to be loaded inside the sheath 4. As shown in FIG. 26, when the cartridge pusher 207 is completely projected out from the distal end of the insertion part 205, the distal end portion of the enlarged-diameter portion 208*b* is elastically deformed and pressed in the inside of the projecting portion 206*b*. The user can confirm the completion of ejecting the marker 101 by feeling resistance at the time of the distal end portion of the enlarged-diameter portion 208*b* being pressed in the inside of the projecting portion 206*b*.

After the marker 101 is loaded inside the sheath 4 thus, the marker 101 is disposed at the disposition site in the same manner as the first embodiment.

In this embodiment, it is possible to easily and reliably load the marker 101 inside the sheath 4 by using the cartridge 202 for loading the marker 101. Furthermore, it is possible to prevent loss of the marker 101 at the time of loading.

Note that although the rod-shaped cartridge pusher 207 is used in this embodiment, the cartridge pusher 207 may be formed in a pipe shape. In this case, since a portion of the marker 101 enters the inner cavity of the pipe, it is possible to push out the marker 101 more reliably.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

Figure 29:
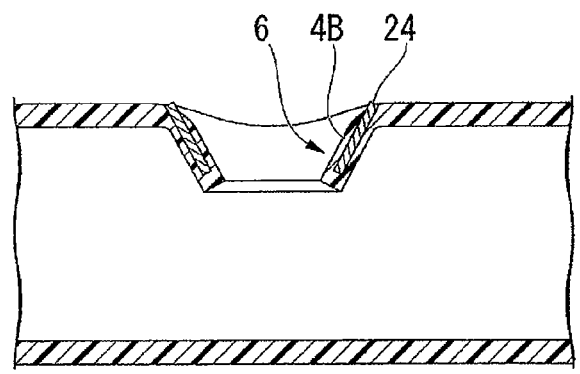
FIG. 29 is a view showing a stopper of a marker disposing tool of a modification of the present invention.

For example, as in the modification shown in FIG. 29, the stopper 6 may be designed so that it can be visually confirmed under fluoroscopy using a method such as embedding a radiopaque material 24 in the inner wall 4B which forms the stopper 6. By providing this design, the user can visually confirm under radioscopy that the marker has passed over the stopper and moved forward. Accordingly, the actions of ejecting and disposing the marker can be carried out with greater certainty.

Figure 30:
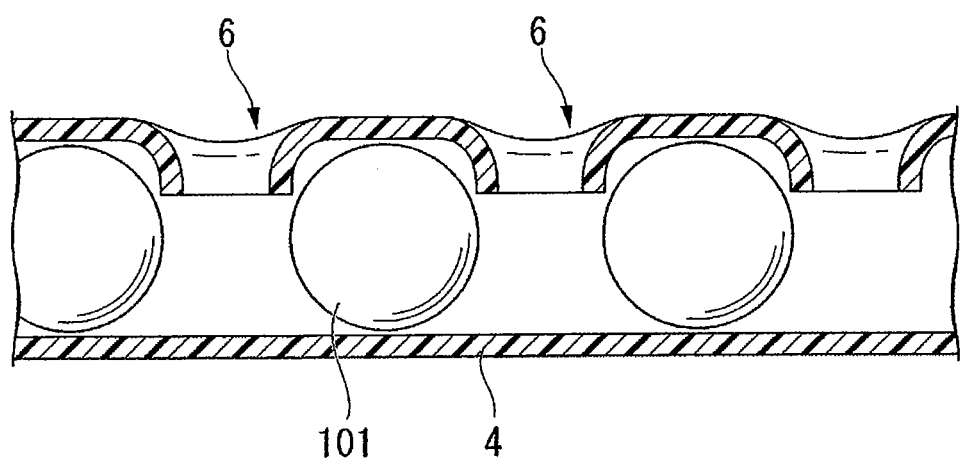
FIG. 30 is a view showing a stopper of a marker disposing tool of a modification of the present invention.

Further, as in the modification shown in FIG. 30, a plurality of stoppers 6 may be provided at specific spacing intervals along the axial direction of the sheath 4. By providing this design, the ejection and disposition of markers 101 can be carried out continuously by preloading multiple markers 101 in the sheath 4. Thus, the efficiency of the procedure can be improved.

The above embodiments discussed an example in which a radiopaque marker was ejected and disposed using a disposing tool. However, it is also acceptable to employ the disposing tool according to the present invention in brachytherapy by ejecting and disposing a capsule-shaped brachytherapy source containing radioactive isotopes or the like.

In addition, the above embodiments discussed an example in which the disposing tool according the present invention was employed in combination with a bronchoscope to dispose a marker for the purpose of radiation treatment of a bronchial tube in the lung. However, in addition to radiation treatment, the disposing tool of the present invention may also be employed for presurgical marker disposition in order identify the incision line for a lung lobectomy using a thoracoscope.

Further, in combination with a thoracoscope or the various other endoscopes, the disposing tool and the medical system according to the present invention may also be used in procedures on organs other than the lungs, such as the liver and prostate.

What is claimed is:

1. An endoscopic medical tool, comprising:
a flexible sheath having an inner cavity;
a member provided in the sheath and configured to be ejected into a body cavity;
an elastically deformable stopper projecting out toward the inner cavity in a distal end portion of the sheath, wherein the stopper is positioned and configured to prevent the member loaded inside the sheath from falling out of the sheath; and
a pusher which is inserted into the sheath so as to advance and to retract freely, and the pusher is positioned and configured to push out and to eject the member from the sheath,
wherein the stopper includes:
a hole penetrating through a surface of the sheath so as to communicate from an outer surface of the sheath into the inner cavity;
said hole is defined by a side wall which is elastically deformable, projects toward the inner cavity in a direction approximately perpendicular to a longitudinal direction of the sheath, and the side wall surrounds the entirety of the hole.

2. The endoscopic medical tool according to claim 1, wherein the stopper is formed in a position except the distal end of the sheath.

3. The endoscopic medical tool according to claim 1, wherein the stopper is formed in the distal end of the sheath; and
the distal end of the sheath is one of an approximately oval shape or polygonal shape extending in a direction perpendicular to the longitudinal direction of the sheath.

4. The endoscopic medical tool according to claim 1, wherein another hole is formed at a position opposite the hole.

5. A medical system which is endoscopically configured to be inserted into a body cavity in order to eject a member into the body cavity, the system comprising:
the endoscopic medical tool according to claim 1; and
a cartridge comprising an insertion part configured to be inserted into the endoscopic medical tool, and the insertion part is configured to house the member.

* * * * *